United States Patent [19]

Kawaguchi et al.

[11] Patent Number: 4,806,524

[45] Date of Patent: Feb. 21, 1989

[54] STABLE ERYTHROPOIETIN PREPARATION AND PROCESS FOR FORMULATING THE SAME

[75] Inventors: Tsutomu Kawaguchi; Naoto Shimoda, both of Saitama, Japan

[73] Assignee: Chugai Seiyaku Kabushiki Kaisha, Tokyo, Japan

[21] Appl. No.: 784,256

[22] Filed: Oct. 3, 1985

[30] Foreign Application Priority Data

Oct. 18, 1984 [JP] Japan .................................. 59-219000

[51] Int. Cl.[4] ............................................. A61K 37/02
[52] U.S. Cl. ........................................ 514/8; 514/970; 530/395
[58] Field of Search ................. 514/8.2, 970; 530/395

[56] References Cited

PUBLICATIONS

Krystal et al., British Journal of Haemotology; vol. 58, No. 3, Nov. 1984, 533–546.

Krystal et al., cited in Chem. Abstracts vol. 102:17774c, 1985.

Primary Examiner—Johnnie R. Brown
Assistant Examiner—Jacqueline M. Stone
Attorney, Agent, or Firm—Morgan & Finnegan

[57] ABSTRACT

A stable erythropoietin preparation and a process for formulating the same are disclosed.

Erythropoietin is useful in the treatment or diagnosis of anemia, but it is an instable substance. In order to provide a stable erythropoietin preparation, it is formulated with one or more stabilizers selected from the group consisting of polyethylene glycols, proteins, sugars, amino acids, inorganic salts, organic salts and sulfur-containing reducing agents.

2 Claims, No Drawings

STABLE ERYTHROPOIETIN PREPARATION AND PROCESS FOR FORMULATING THE SAME

BACKGROUND OF THE INVENTION

The present invention relates to a stable erythropoietin preparation and a process for formulating the same.

Erythropoietin is a circulating glycoprotein that stimulates the formation of red blood cells and is useful in the treatment or diagnosis of anemia. A single dose of erythropoietin is as small as a few micrograms and this level must be strictly observed. In other words, erythropoietin must be administered in the acurately measured trace amount in which it is formulated in a dosage form. However, erythropoietin is an instable substance and the compound purified to a clinically acceptable level and formulated in a trace amount ($\simeq$ a few $\mu g$) that is suitable for a single dosage will be easily inactivated by such environmental factors as temperature and humidity. It is therefore desired to formulate erythropoietin in a stabilized form.

As a result of various studies made in order to formulate a stable erythropoietin preparation, the present inventors found that this object can be attained by mixing erythropoietin with a particular compound. The present invention has been accomplished on the basis of this finding.

SUMMARY OF THE INVENTION

In accordance with one aspect of the present invention, an erythropoietin preparation is provided that contains one or more stabilizers selected from the group consisting of polyethylene glycol, protein, sugar, amino acid, inorganic salt, organic salt and sulfur-containing reducing agent.

In accordance with another aspect of the invention, a process is provided for formulating a stable erythropoietin preparation containing one or more of the stabilizers listed above.

DETAILED DESCRIPTION OF THE INVENTION

The only requirement for the erythropoietin preparation in accordance with one aspect of the present invention is that at least one of the stabilizers listed above be mixed with erythropoietin. This erythropoietin preparation may be formulated in any dosage form such as a liquid dosage form, a solid dosage form (e.g. tablet, capsule, fine granule, granule or powder), or semisolid dosage form (e.g. suppository).

In accordance with the present invention, the erythropoietin may be obtained by any known method; it may be extracted from human urine, followed by separation and purification; alternatively it may be produced in E. coli, yeasts or Chinese hamsters ovary cells by genetic engineering technology, and extracted from the culture by a variety of methods, followed by separation and purification. The dosage of erythropoietin varies with the object of a specific diagnosis or treatment, and formulations containing 0.1-50 $\mu g$ of erythropoietin per unit dosage form may be used. It should however be noted that the present invention is not limited by the erythropoietin content.

Proteins used as erythropoietin stabilizers include bovine serum albumin and gelatin; sugars include monosaccharides such as xylose, mannose, glucose and fructose, disaccharides such as lactose, maltose and sucrose, trisaccharides such as raffinose, polysaccharides such as dextran, sugar alcohols such as mannitol, sorbitol and glycerol, and cyclitols such as inositol; amino acids include glycine, alanine and lysine; inorganic salts include potassium chloride, calcium chloride, sodium phosphate, potassium phosphate and sodium hydrogencarbonate; organic salts include sodium citrate, potassium citrate and sodium acetate; and sulfur-containing reducing agents include glutathione, thioctic acid, sodium thioglycolate, thioglycerol, $\alpha$-monothioglycerol and sodium thiosulfate.

These stabilizers are preferably incorporated in amounts of 0.1-10,000 parts by weight per part by weight of erythropoietin. Two or more of these stabilizers may be used if their total amount is within this range.

Erythropoietin may be administered by various routes such as injection (e.g. iv or mv), oral administration into digestive tracts, and transmucous administration directed to the mucous of the rectum, oral cavity or nasal cavity. Dosage forms suitable for the administration of erythropoietin include a liquid dosage form (e.g. injection), a solid dosage form (e.g. tablet, capsule, fine granule, granule or powder), and semisolid dosage form (e.g. suppository). Any conventional pharmaceutical additive may be mixed with erythropoietin as well as the stabilizers falling within the scope of the present invention so long as its stability is not impaired.

In order to prepare an erythropoietin injection, the stabilizer is used in the form of an aqueous solution having the proper concentration and pH. The osmotic pressure ratio of this aqueous solution is generally in the range of 0.1-3.0, preferably 1.0. The pH of the aqueous solution is generally adjusted to be within the range of 5.0-9.0, preferably 6.0-8.0. An anti-adsorption agent is preferably used in formulating the erythropoietin preparation of the present invention in the form of a solution such as injection, or when handling erythropoietin in the liquid state during formulation.

The following Experiments and Examples are provided for the purpose of further illustrating the present invention.

EXPERIMENTS (1) Erythropoietin derived from human urine (0.1 mg) was dissolved in 200 ml of 0.01% lecithin suspension and 5-ml portions of the solution were charged into test tubes. The stabilizers shown in the following table were put into the test tubes in the amounts also indicated in the table. Each of the mixtures was distributed among 10 vials in amounts of 0.5 ml and freeze-dried. The 10 vials were divided into two groups, each consisting of 5 vials. The freeze-dried mixtures of one group were immediately dissolved in an aqueous solution containing 0.1% bovine serum albumin, 0.15M NaCl and 0.01M CaCl$_2$, and the mixtures of the other group were left to stand at 37° C. for one month before they were dissolved in the same solution. The activity of erythropoietin in each group was measured by the fasted rat method described in Goldwasser, E. and Gross, M., Methods in Enzymol., vol. 37, pp. 109-121 (1975). The percentage of residual activity was determined, with the value for the first group (dissolved in aqueous solution immediately after freeze-drying) being taken as 100. The results are shown in the following table in the column of "Percentage of residual activity—Freeze-dried". Each of the figures in the column was a mean of five measurements. The data in the table show the effectiveness of the stabilizing agents specified by the present invention.

(2) Erythropoietin derived from human urine (0.1 mg) was dissolved in 200 ml of 0.01% lecithin suspension and 5-ml portions of the solution were charged into test tubes. The stabilizers shown in the following table were put into the test tubes in the amounts also indicated in the table. Each of the mixtures was distributed among 10 vials in amounts of 0.5 ml. The vials were divided into two groups, each consisting of 5 vials. The activity of erythropoietin in the first group was immediately measured by the same fasted rat method that was used in Experiment (1), whereas the activity of erythropoietin in the second group was measured by the same method after standing at 25° C. for one week. The percentage of residual activity was determined, with the average value for the first group being taken as 100. The results are shown in the following table in the column of "Percentage of residual activity—Aqueous solution". The data show that the stabilizers in accordance with the present invention are also effective in stabilizing the activity of erythropoietin in an aqueous solution.

TABLE

| Stabilizer | Amount of stabilizer per part by weight of erythropoietin | Percentage of residual activity Freeze-dried | Percentage of residual activity Aqueous solution |
| --- | --- | --- | --- |
| Polyethylene glycol 4000 | 50 | 94 | 71 |
| Gelatin | 100 | 96 | 73 |
| Dextran 40 | 50 | 98 | 70 |
| Glycerol | 100 | 95 | 67 |
| Mannitol | 100 | 95 | 69 |
| Sorbitol | 100 | 93 | 62 |
| Inositol | 100 | 98 | 71 |
| Glucose | 100 | 90 | 64 |
| Fructose | 100 | 93 | 65 |
| Xylose | 100 | 93 | 68 |
| Mannose | 100 | 99 | 71 |
| Maltose | 100 | 97 | 76 |
| Sucrose | 100 | 96 | 70 |
| Raffinese | 100 | 91 | 66 |
| Glycine | 100 | 96 | 75 |
| Alanine | 100 | 98 | 77 |
| Lysine | 100 | 88 | 63 |
| NaCl | 100 | 92 | 61 |
| KCl | 100 | 89 | 71 |
| $CaCl_2$ | 100 | 99 | 67 |
| Potassium dihydrogenphosphate Disodium hydrogenphosphate.$2H_2O$ | 36.2 71.4 | 92 | 67 |
| Potassium dihydrogenphosphate Sodium hydrogencarbonate | 28.8 69.9 | — | 69 |
| Acetic acid Sodium acetate.$3H_2O$ | 0.6 87.0 | — | 69 |
| Sodium dihydrogen-phosphate.$2H_2O$ Citric acid.$2H_2O$ | 97.7 12.3 | 87 | 70 |
| Glutathione | 10 | 90 | 66 |
| Thioctic acid | 10 | 90 | 67 |
| Na salt of thioglycolic acid | 10 | 89 | 68 |
| Thioglycerol | 10 | 87 | 65 |
| α-monothioglycerol | 10 | 89 | 67 |
| Na salt of thiosulfuric acid | 10 | 88 | 68 |
| None | 0 | 60 | 46 |

EXAMPLE 1

Erythropoietin: 1 part by weight
Gelatin: 100 parts by weight
Distilled water for injection to make: $10^5$ parts by weight An aqueous solution having the above composition was aseptically prepared, distributed among vials and freeze-dried, followed by the hermetic sealing of the vials.

EXAMPLE 2

A freeze-dried erythropoietin preparation was formulated as in Example 1 except that 100 parts by weight of gelatin was replaced by an equal amount of dextran 40.

EXAMPLE 3

A freeze-dried erythropoietin preparation was formulated as in Example 1 except that 100 parts by weight of gelatin was replaced by 500 parts by weight of polyethylene glycol 4000.

EXAMPLE 4

Erythropoietin: 1 part by weight
Human serum albumin: 50 parts by weight
Glycine: 200 parts by weight
Mannitol: 500 parts by weight
Distilled water for injection to make: $10^5$ parts by weight An aqueous solution having the above composition was aseptically prepared, distributed among vials and freeze-dried, followed by the hermetic sealing of the vials.

EXAMPLE 5

A freeze-dried erythropoietin preparation was formulated as in Example 4 except that the glycine and mannitol were replaced by 200 parts by weight of gelatin and 500 parts by weight of $CaCl_2$.

EXAMPLE 6

Erythropoietin: 1 part by weight
Glutathione: 10 parts by weight
Human serum albumin: 50 parts by weight
Glucose: 500 parts by weight
Distilled water for injection to make: $10^5$ parts by weight An aqueous solution having the above composition was aseptically prepared, distributed among vials and freeze-dried, followed by the hermetic sealing of the vials.

EXAMPLE 7

A freeze-dried erythropoietin preparation was formulated as in Example 6 except that the glutathione and glucose were replaced by 10 parts by weight of thioglycerol and 500 parts by weight of maltose.

EXAMPLE 8

Erythoropoietin: 1 part by weight
Dextran 40: 50 parts by weight
NaCl: 500 parts by weight
Disodium hydrogenphosphate.$2H_2O$: 140 parts by weight
Potassium dihydrogenphosphate: 70 parts by weight
Distilled water for injection to make: $10^5$ parts by weight An aqueous solution having the above composition was aseptically prepared and distributed among ampules which were then sealed by fusing.

EXAMPLE 9

An ampule solution was prepared as in Example 8 except that the disodium hydrogenphosphate, potassium dihydrogenphosphate and NaCl were replaced by 98 parts by weight of sodium dihydrogenphosphate.2-$H_2O$, 12 parts by weight of citric acid monohydrate and 500 parts by weight of sucrose.

EXAMPLE 10

Nineteen parts by weight of Novata E (suppository base of Henkel, Inc.) was dissolved in water at 40°-60° C., followed by gradual cooling. When the temperature of the solution reached 40° C., it was mixed with one part by weight of a separately prepared aqueous solution of erythropoietin (containing 0.001 wt% of erythropoietin, 0.5 wt% of polyethylene glycol 4000 and 5 wt% of Nikkol BL9EX, or a surfactant produced by Nikko Chemicals K.K.) and an intimate mixture was obtained under agitation. The resulting mixture was poured into containers in amounts of about 2 g and cooled to solidify as suppositories.

EXAMPLE 11

A mixture of mannitol (5,000 parts by weight), erythropoietin (1 part by weight), human serum albumin (100 parts by weight), sodium acetyltryptophanate (2.154 parts by weight) and sodium caprylate (1.33 parts by weight) was dissolved in purified water to make a total of $10^5$ parts by weight, and the resulting aqueous solution was freeze-dried. The freeze-dried product was charged into capsules specified in the Japanese Pharmacopoeia, which were covered with an enteric coating agent by a known method, so as to make enteric capsules.

What is claimed is:

1. An erythropoietin preparation containing one or more protein stabilizers selected from the group consisting of bovine serum albumin, human serum albumin and gelatin.

2. A process for formulating an erythropoietin preparation by mixing erythropoietin with one or more protein stabilizers selected from the group consisting of bovine serum albumin, human serum albumin and gelatin.

* * * * *